United States Patent
Backes

(10) Patent No.: US 7,721,598 B2
(45) Date of Patent: May 25, 2010

(54) METHOD AND SENSOR FOR DETECTING OCCURRENCES OF WETTING ON A PANE

(75) Inventor: Ulrich Backes, Radolfzell (DE)

(73) Assignee: TRW Automotive Electronics & Components GmbH, Radolfzell (DE)

( * ) Notice: Subject to any disclaimer, the term of this patent is extended or adjusted under 35 U.S.C. 154(b) by 96 days.

(21) Appl. No.: 12/156,675

(22) Filed: Jun. 3, 2008

(65) Prior Publication Data

US 2008/0307878 A1  Dec. 18, 2008

(30) Foreign Application Priority Data

Jun. 12, 2007  (DE) .................. 10 2007 027 071

(51) Int. Cl.
*G01W 1/00* (2006.01)
(52) U.S. Cl. .................................. 73/170.17
(58) Field of Classification Search .............. None
See application file for complete search history.

(56) References Cited

U.S. PATENT DOCUMENTS

| | | | | | |
|---|---|---|---|---|---|
| 5,528,224 | A | * | 6/1996 | Wang | 340/583 |
| 5,539,289 | A | | 7/1996 | Wiget | |
| 6,114,950 | A | * | 9/2000 | Schaible et al. | 340/435 |
| 6,331,819 | B1 | | 12/2001 | Hog | |
| 6,341,523 | B2 | * | 1/2002 | Lynam | 73/170.17 |
| 6,369,378 | B1 | * | 4/2002 | Lamm et al. | 250/227.25 |
| 6,516,664 | B2 | * | 2/2003 | Lynam | 73/170.17 |
| 6,634,225 | B1 | | 10/2003 | Reime | |
| 6,744,371 | B1 | * | 6/2004 | Schmitt et al. | 340/602 |
| 6,968,736 | B2 | * | 11/2005 | Lynam | 73/170.17 |
| 7,380,980 | B2 | * | 6/2008 | Kanai et al. | 374/19 |
| 2003/0183752 | A1 | * | 10/2003 | Kobayashi et al. | 250/222.2 |

FOREIGN PATENT DOCUMENTS

| | | |
|---|---|---|
| DE | 19723859 | 12/1998 |
| DE | 19740364 | 3/1999 |
| DE | 19860214 | 7/2000 |
| DE | 10019112 | 8/2001 |
| DE | 10219690 | 11/2003 |
| EP | 0460180 | 12/1991 |
| EP | 0849609 | 6/1998 |
| EP | 1641013 | 3/2006 |

* cited by examiner

*Primary Examiner*—Lisa M Caputo
*Assistant Examiner*—Jermaine Jenkins
(74) *Attorney, Agent, or Firm*—Tarolli, Sundheim, Covell & Tummino LLP

(57) ABSTRACT

The method operates with successive, continuously repeated measuring cycles. In a first cycle section, a measuring capacitor is charged up to a first threshold value by the current flowing in a light receiver of a first optical measuring section. In a subsequent, second cycle section the measuring capacitor is discharged to a second threshold value by the current flowing in a light receiver of a second optical measuring section. The light transmitters of the optical measuring sections are regulated over several measuring cycles to predetermined rated values for the charging time and the discharging time. A wetting of the pane is concluded from the momentary deviations between the rated values and the actually measured values of the charging times and discharging times. The available modulation range is adapted dynamically to the prevailing conditions by the systematic control of the intensity of the light transmitters in the two optical measuring sections. In addition, the upper limit of the modulation range is extended to higher values of the ambient light.

10 Claims, 2 Drawing Sheets

METHOD AND SENSOR FOR DETECTING OCCURRENCES OF WETTING ON A PANE

BACKGROUND OF THE INVENTION

The invention relates to a method and a sensor for detecting occurrences of wetting on a pane, particularly a rain sensor for vehicles.

Rain sensors have optical measuring sections which contain a light transmitter and a light receiver. Light transmitters and light receivers are coupled to the inner side of the pane so that light emitted from the light transmitter is reflected onto the light receiver by total reflection on the outer surface of the pane. However, the light receiver is also exposed to the ambient light. In order to reduce the influence of the ambient light, two identical optical measuring sections can be used which are arranged adjacent to each other, with the differential signal of the light receivers then being evaluated. However, the modulation capability is limited by outside light and the asymmetry of the optical and electronic components.

SUMMARY OF THE INVENTION

The present invention provides a method and a sensor for detecting occurrences of wetting on a pane, by which the usable modulation range and the detection sensitivity are increased.

The method according to the invention operates with successive, continuously repeated measuring cycles. In a first cycle section, a current/voltage transformer, which can be formed by a measuring capacitor, is charged by the current flowing in a light receiver of a first optical measuring section up to a first threshold value. In a subsequent second cycle section, the measuring capacitor is discharged by the current flowing in a light receiver of a second optical measuring section to a second threshold value. The light transmitters of the optical measuring sections are closed-loop regulated over several measuring cycles to predetermined rated values for the charging time and the discharging time. A conclusion is finally drawn with regard to the wetting of the pane from the instantaneous deviations between the rated values and actually measured values of charging times and discharging times. The available modulation range is adapted dynamically to the prevailing conditions by the systematic control of the intensity of the light transmitters in the two optical measuring sections. In addition, the upper limit of the modulation range is extended to higher values of the ambient light.

The sensor according to the invention for detecting occurrences of wetting on a pane has two optical measuring sections which are able to be coupled to the pane, each of which has a controllable light transmitter and a light receiver. The sensor further comprises a comparator, the first input of which is connected with a measuring capacitor and at the second input of which one or other of two threshold values is applied selectively by means of a change-over switch. A control circuit controls the light transmitters alternately. In addition, the control circuit connects the measuring capacitor selectively with the light receivers via a controllable switch. The control circuit, for example a programmed micro-controller or an application-specific integrated circuit (ASIC) carries out a sequence control such that in continuously repeated measuring cycles, respectively in a first cycle section the measuring capacitor is charged by the current flowing in the light receiver of the first optical measuring section up to the first threshold value, and in a subsequent second cycle section the measuring capacitor is discharged by the current flowing in the light receiver of the second optical measuring section to the second threshold value. The light transmitters of the two optical measuring sections are closed-loop regulated over several measuring cycles to predetermined rated values for the charging time and the discharging time. A wetting of the pane is detected based on instantaneous deviations between the rated values and actually measured values of charging times and discharging times, and a corresponding control signal is provided, for example a control signal for the windscreen wiper system of a vehicle.

Advantageous further developments of the invention are indicated in the sub-claims.

DESCRIPTION OF PREFERRED EMBODIMENT

Further features and advantages of the invention will be apparent from the following description of an advantageous embodiment with reference to the enclosed drawings, in which.

Figure 1:
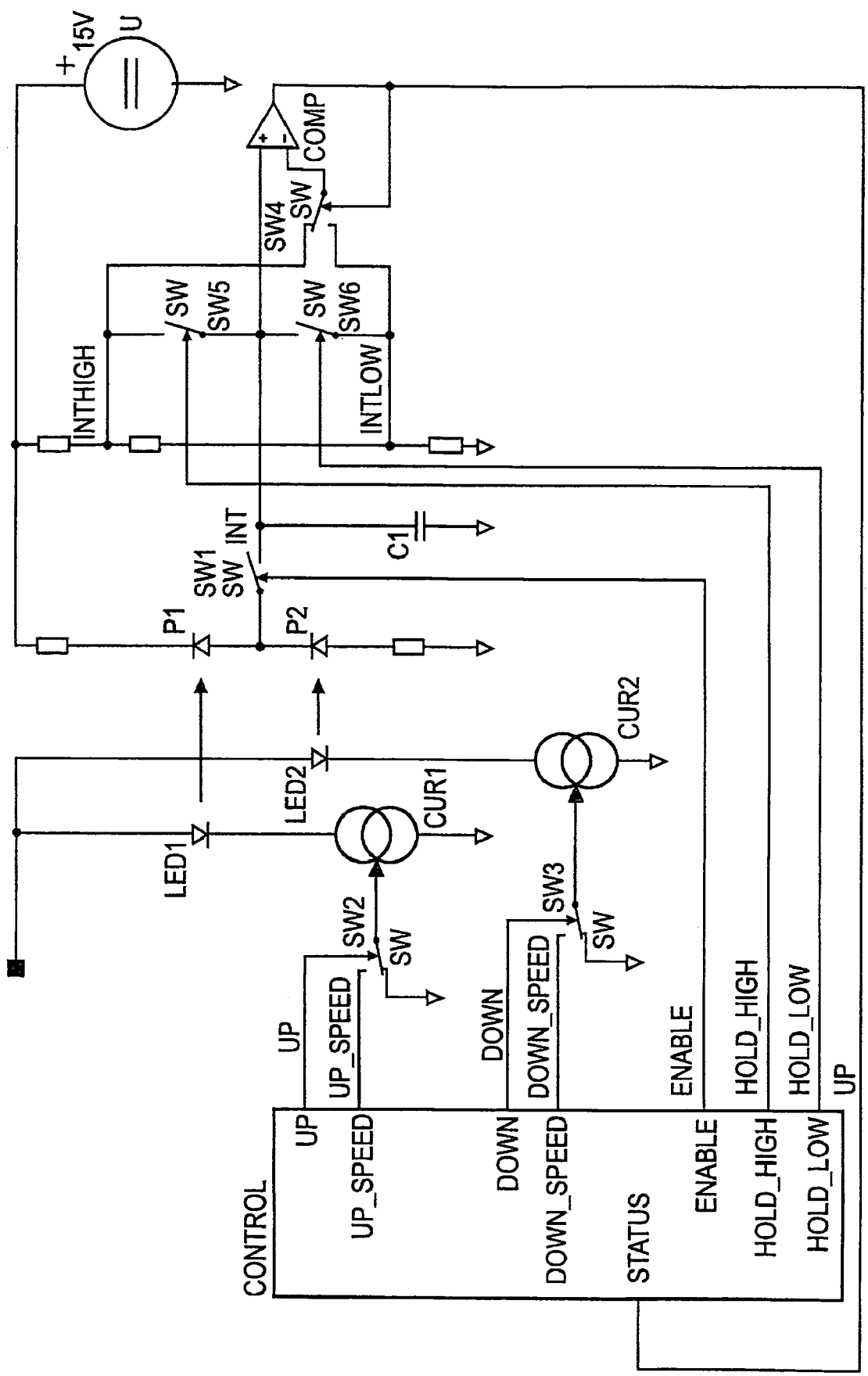
FIG. 1 shows diagrammatically a circuit diagram of a sensor.

The sensor contains two optical measuring sections which are coupled to the inner surface of the pane. The first optical measuring section consists of a light transmitter LED1 in series with a controllable current source CUR1, and a light receiver P1. The second optical measuring section consists of a light transmitter LED2 in series with a controllable current source CUR2, and a light receiver P2. The association between light transmitters and light receivers is symbolized in FIG. 1 respectively by an arrow. The light receivers P1, P2 are arranged in series with each other and with two resistances symmetrically between the two poles of a constant voltage source U. A measuring capacitor C1 is able to be connected by means of a controllable switch SW1 with the connection point between the light receivers P1, P2. The measuring capacitor C1 is additionally connected with the non-inverting input of a comparator COMP, the inverting input of which can be connected via a change-over switch SW4 with one or other of two fixed threshold values INTHIGH and INTLOW. The two fixed threshold values INTHIGH and INTLOW are derived by means of a resistive voltage divider from the constant voltage source U. The change-over switch SW4 is controlled by the output signal STATUS of the comparator COMP.

In the simple embodiment which is shown, the measuring capacitor C1 is used for the integration of the current flow in the light receivers. This measuring capacitor has the function of a current/voltage transformer. In actual implementation, a current/voltage transformer is used with an additional filter and a separate integration circuit.

A control circuit CONTROL controls the current source CUR1 of the first optical measuring section and the current source CUR2 of the second optical measuring section. To do this, the control circuit connects the control input of the current source CUR1 via a change-over switch SW2 either with signal ground or with a control signal UP_SPEED. In an analogous manner, the control circuit applies either the ground signal or a control signal DOWN_SPEED at the control input of the current source CUR2 via a change-over switch SW3. The change-over switch SW2 is controlled by the signal UP and the change-over switch SW3 is controlled by the signal DOWN. The control circuit CONTROL, to which the output signal STATUS of the comparator COMP is supplied as an input signal, controls the controllable switch SW1 with a signal ENABLE.

The control circuit CONTROL, for example a programmed microcontroller or an application-specific integrated circuit ASIC, is designed so that it carries out the sequence control which is described in further detail below with the aid of FIG. 2.

Figure 2:
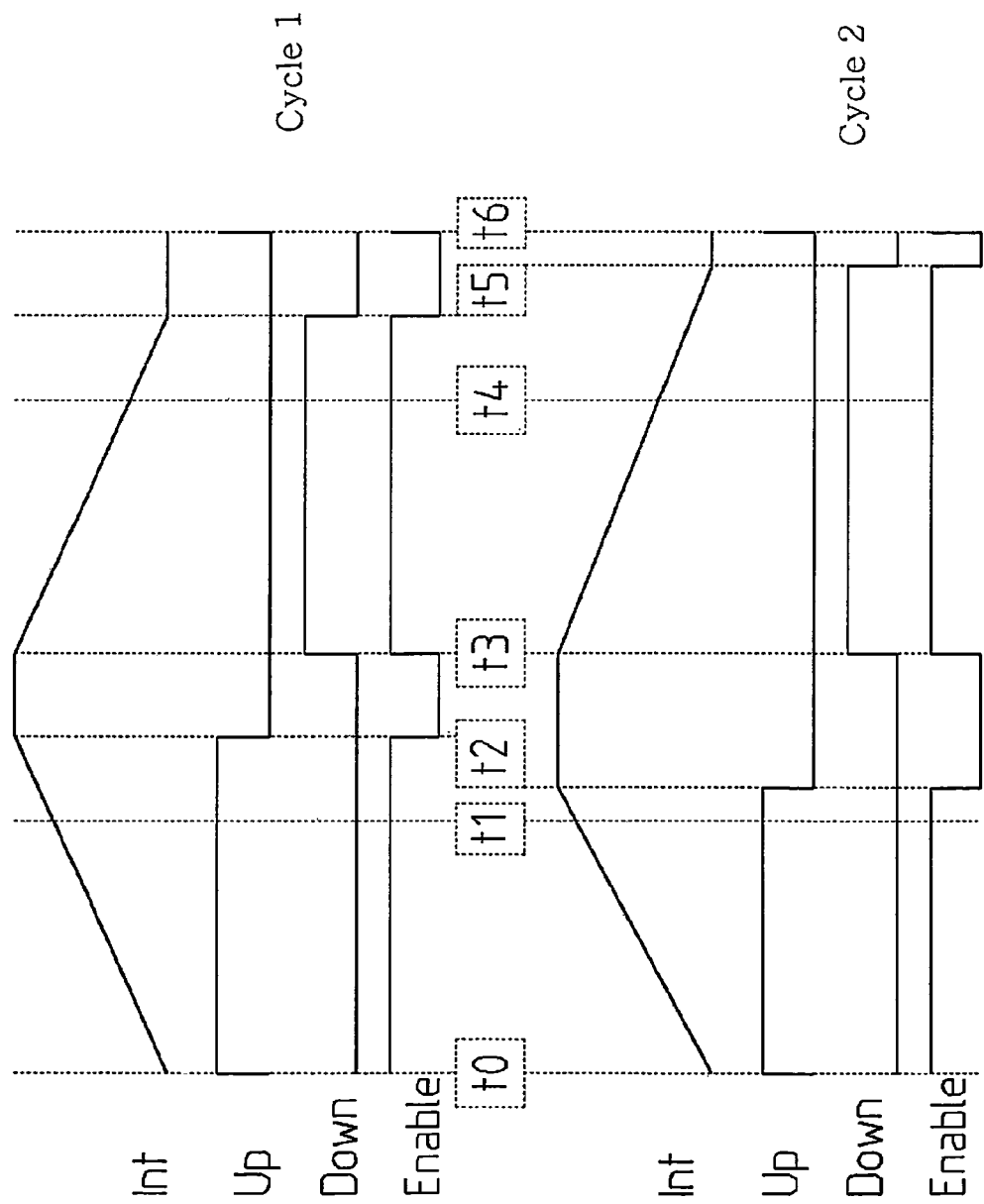
FIG. 2 shows a signal diagram which illustrates the mode of operation of the sensor.

In FIG. 2, firstly "cycle 1" is considered. The sequence consists of continuously repeated measuring cycles. At the start of a measuring process, the measuring capacitor C1 is charged by means of a switch SW6 to the lower threshold value INTLOW. Alternatively, the measuring capacitor C1 can be charged to the upper threshold value INTHIGH at the start by means of a switch SW5. In the diagram of FIG. 2, however, it is assumed that the cycle begins with a charging process. At the moment t0, the change-over switch SW2 is controlled by the signal UP, in order to connect the control input of the current source CUR1 with the control signal UP_SPEED. This control signal UP_SPEED is set to a suitable default value at the start of the measuring process. At the same time, the switch SW1 is closed by the control signal ENABLE. The light originating from the light transmitter LED1 falls onto the light receiver P1, in which a current flows, by which the measuring capacitor C1 is charged. At the moment t2, the voltage INT at the measuring capacitor C1 reaches the upper threshold value INTHIGH. The comparator COMP changes over and delivers the signal STATUS to the control circuit CONTROL, whereby the control signal ENABLE is terminated. With the start of the charging process at the moment t0, the control circuit starts an internal counter or timer which it stops on completion of the charging process at the moment t2. After a short pause, the current source CUR1 is deactivated at the moment t3 and the current source CUR2 is activated, by the change-over switch SW3 being reversed by the control signal DOWN and the current control signal DOWN_SPEED being thus applied to the control input of the current source CUR2. The light receiver P2 is now provided with current by the light originating from the light transmitter LED2, so that the measuring capacitor C1 is discharged. The voltage INT at the measuring capacitor C1 reaches the lower threshold value INTLOW at the moment t5, so that the comparator COMP switches back. As previously, a counter or timer is started in the control circuit CONTROL at the start of the discharging process at the moment t3, and is stopped at the end of the discharging time at the moment t5. In the subsequent short pause between the moments t5 and t6, an evaluation takes place of the counter readings or timer values in the control circuit CONTROL. A constant cycle duration is achieved by the pause.

Rated values are predetermined internally in the control circuit for the charging time and the discharging time. The actually measured charging times and discharging times are compared with the predetermined rated values. When a deviation is detected, the current control signals UP_SPEED and DOWN_SPEED are re-adjusted for the purposes of regulation. This closed-loop regulation takes place relatively slowly over a plurality of measuring cycles. Momentary deviations between the rated values and the charging and discharging times are interpreted as a disturbance to the balance between the two optical measuring sections, particularly as a wetting of the pane.

Whereas in FIG. 2 the "cycle 1" is symmetrical, i.e. the charging time is approximately equal to the discharging time, "cycle 2" constitutes a non-symmetrical measuring cycle. The longer discharging time, compared with the charging time, leads to the conclusion that there is a wetting on the second optical measuring section.

The invention claimed is:

1. A method for detecting occurrences of wetting on a pane, particularly the windscreen of a vehicle, in which in successive, continuously repeated measuring cycles:
    a) in a first cycle section, a current flowing in a light receiver of a first optical measuring section is integrated up to a first threshold value;
    b) in a second cycle section, a current flowing in a light receiver of a second optical measuring section is integrated to a second threshold value;
    c) the optical measuring sections have light emitters which are closed-loop regulated over a plurality of measuring cycles to obtain predetermined rated values of the integration times; and
    d) detecting a wetting of the pane based on momentary deviations between the rated values and actually measured values of the integration times.

2. The method according to claim 1, in which at the start of a measuring process an initialization is carried out, in which the light transmitters are set to an initial value of light intensity.

3. The method according to claim 2, in which the integration takes place by charging and discharging a measuring capacitor, which is charged on initialization to one of the threshold values.

4. The method according to claim 1, in which a pause is included between successive cycle sections.

5. A sensor for detecting occurrences of wetting on a pane, particularly the windscreen of a vehicle, with
    two optical measuring sections which are adapted to be coupled to the pane, each of which has a controllable light transmitter (LED1, LED2) and a light receiver (P1, P2);
    a current/voltage transformer (C1);
    a comparator (COMP), which has a first input (+) connected with the current/voltage transformer, and a second input (−) to which one out of two threshold values (INTHIGH, INTLOW) is applied selectively by means of a change-over switch (SW4); and
    a control circuit (CONTROL), which controls the light transmitters (LED1, LED2) alternately and connects the current/voltage transformer (C1) selectively with the light receivers (P2, P2) by means of a controllable switch (SW1);
    in which the control circuit (CONTROL) controls a sequence of successive, continuously repeated measuring cycles:
    a) in a first cycle section (t0-t2) the current/voltage transformer (C1) integrates a current flowing in the light receiver (P1) of the first optical measuring section up to the first threshold value (INTHIGH);
    b) in a second cycle section the current/voltage transformer (C1) integrates a current flowing in the light receiver (P2) of the second optical measuring section to the second threshold value (INTLOW);
    c) the light transmitters (LED1, LED2) of the optical measuring sections are closed-loop regulated over a plurality of measuring cycles to obtain predetermined rated values of the integration times; and
    d) wetting of the pane is detected based on momentary deviations between the rated values and actually measured values of the integration times.

6. The sensor according to claim 5, in which the light receivers (P1, P2) of the optical measuring sections are connected symmetrically in series between two fixed voltage potentials.

7. The sensor according to claim 6, in which the measuring capacitor is adapted to be connected with the interconnection node of the light receivers (P1, P2) by means of the controllable switch (SW1).

8. The sensor according to claim 5, in which the light transmitters (LED1, LED2) are each arranged in series with a controllable current source (CUR1, CUR2).

9. The sensor according to claim 5, in which the change-over switch is controlled by the output signal (STATUS) of the comparator (COMP).

10. The sensor according to claim 5, in which the current/voltage transformer is formed by a measuring capacitor (C1) which can be charged to one of the threshold values (INTHIGH, INTLOW) by means of a switch (SW5, SW6) which is able to be controlled by the control circuit (CONTROL).

* * * * *